United States Patent [19]

Schmid

[11] 4,454,070

[45] Jun. 12, 1984

[54] TRANSITION METAL-COMPLEX COMPOUNDS AND METHOD FOR MAKING THE SAME

[75] Inventor: Gunter Schmid, Velbert, Fed. Rep. of Germany

[73] Assignee: Wacker-Chemie GmbH, Munich, Fed. Rep. of Germany

[21] Appl. No.: 381,358

[22] Filed: May 24, 1982

[30] Foreign Application Priority Data

Jun. 3, 1981 [DE]  Fed. Rep. of Germany ....... 3121927

[51] Int. Cl.³ .............................................. C07F 15/00
[52] U.S. Cl. ............................... 260/429 R; 260/430; 260/439 R; 260/438.5 R
[58] Field of Search ............ 260/429 R, 430, 438.5 R, 260/439 R

[56] References Cited

U.S. PATENT DOCUMENTS

| | | | |
|---|---|---|---|
| 3,676,554 | 7/1972 | McGusty et al. ................ | 260/430 X |
| 4,012,399 | 3/1977 | Hechenbleikner et al. .... | 260/429 R X |
| 4,190,595 | 2/1980 | Diamond et al. ............... | 260/429 R |
| 4,196,135 | 4/1980 | Enomoto et al. ............... | 260/429 R |
| 4,199,520 | 4/1980 | Cosby et al. .................... | 260/429 R |

*Primary Examiner*—Helen M. S. Sneed
*Attorney, Agent, or Firm*—Collard, Roe & Galgano

[57] ABSTRACT

The invention relates to a novel transition metal-complex compounds of the general formula $M_{55}L_{12}X_p$, wherein M is a transition metal of one of the subgroups I, V, VI, VII, or VIII, of the Periodic System of the Elements, L stands for ligands having electron donor properties, X is halogen, and p is equal to 6 to 20. The novel compounds are prepared by reaction of the complex compounds of the formula $L_nMX_m$, wherein n represents an integer from 1 to 5, and m an integer from 1 to 4, with compounds of the general formula EHRR', wherein E stands for aluminum or boron, R and R' can be equal or different, and represent hydrogen or straight-chain or branched chain hydrocarbon radicals having from 1-10 carbon atoms.

2 Claims, No Drawings

TRANSITION METAL-COMPLEX COMPOUNDS AND METHOD FOR MAKING THE SAME

The invention relates to transition metal-complex compounds and a process for making the same, forming so-called transition metal clusters of exceptional size.

The largest hitherto known and isolated transition metal clusters contain up to 38 metal atoms and carry as ligands, especially carbon monoxide; see e.g. $(Rh_{15}(CO)_{27})^{3-}$, S. Martinengo et al, *J. Amer. Chem. Soc.* 100, 7096 (1978); $(Rh_{17}(CO)_{32}S_2)^{3-}$, J. Vidal et al., *Inorg. Chem.* 17, 2574 (1978); $(Rh_{22}(CO)_{37})^{4-}$, S. Martinengo et al, *J. Amer. Chem. Soc.* 102, 7564 (1980); $(Pt_{19}(CO)_{22})^{4-}$, D. M. Washechek et al, *J. Amer. Chem. Soc.* 101, 6110 (1979).

Gold clusters of the formula $Au_{11}L_7X_3$ and $(Au_{13}(LL)_6)^{4+}$ (L=phosphane, LL=diphosphane, X=halogen, pseudohalogen (F. Cariati and L. Naldini, *Inorgan. Chim. Acta* 5 1972, 1481) (P. L. Ballon, M. Manassero and M. Sansoni, *J. Chem. Soc.*, Dalton 1972, 1481) contain for the first time more metal atoms than ligands. The 10 or 12 peripheral gold atoms form only one terminal phosphane- or halogen- or pseudohalogen-ligand each. The eleventh (or thirteenth) gold atom is located in the center of an incomplete (or complete) icosahedron. For clusters in closest spherical packing, the proportion of surface atoms becomes less and less with increasing total number of metal atoms. Thus, it can be calculated that the proportion of surface atoms decreases from 100% for 4 or 6 atoms, 92% for 13 atoms (smallest possible cuboctahedron) and 52% for 309 atoms down to 15% for 21,127 atoms. From the view point of catalytic action, it appears desirable to make such clusters, which in their properties lie between the known complex catalysts with one or a few (maximally 38) metal atoms and the purely metallic catalysts. There are no known synthesis methods for preparing catalysts of this kind.

It is therefore an object of the present invention to discover such compounds and provide syntheses for their preparation.

The problem was solved according to the invention by using transition metal-complex compounds of the general formula $M_{55}L_{12}X_p$ wherein M is a transition metal of subgroup I, V, VI, VII, or VIII of the Periodic System of Elements of Mendeljeff (see *Handbook of Chemistry and Physics*, 55th edition 1974-1975, CRC-Press, printed on the inside of the bound volume); L stands for ligands having electron donor properties, X is halogen and p is equal to an integer 6 to 20.

The novel compounds can be prepared according to the invention by a process which consists in reacting complex compounds of the general formula $L_nMX_m$, wherein M, L and X have the meaning defined above, n is an integer from 1 to 5 and m is an integer from 1 to 4, with compounds of the general formula EHRR', wherein E stands for aluminum or boron, and R as well as R' represent H or straight-chain or branched chain hydrocarbon radicals with 1-10 carbon atoms; R and R' may be the same or different radicals.

For ligands with electrondonor properties molecules are generally understood, which have $\pi$-electron pairs or free electron pairs, e.g., carbon monoxide, amines, phosphines, diphosphines, arsines, diarsanes, phosphites, stibines, stannane, etc. The size of the ligands in reference to the atom radius of the metal atom of these novel transition metal-complex compounds plays a certain role as regards the stability of the complex compounds. For instance, a rhodium-cluster with tritertiary butylphosphine is more stable than a rhodium-cluster with trimethyl phosphite as ligand, whereas the case is exactly reversed with the smaller nickel.

For example, compounds of gold, vanadium, chromium, molybdenum, manganese, cobalt, nickel, ruthenium, rhodium or palladium are easily prepared.

The reaction of the above defined complex compounds $L_nMX_m$ to form the new transition metal-complex compounds according to the invention is carried out under protective gas, e.g. argon or nitrogen, and advantageously in a solvent, preferably aromatics, such as benzene, toluene or pyridine; other suitable solvents are methylene chloride or ether, and especially tetrahydrofuran. The aluminum or boron hydrides, or organically substituted compounds of the likewise defined general formula EHRR' are introduced into the solution of the complex compounds $L_nMX_m$, the operation being preferably carried out at temperatures between room temperature and the boiling temperature of the solvent used, thus approximately in a temperature range of 20°–120° C. The new compounds are partly precipitated directly in finely crystallized form and can be filtered off for separation. But it is more often advantageous to distill off the solvent carefully under reduced pressure and to add to the remaining oily residue, which is more or less intensely colored, a non-polar solvent, e.g., benzine, and to re-crystallize the solid body formed, and thereafter separate it. In principle, the reaction can be carried out continuously or discontinuously.

The novel transition metal clusters are highly active catalysts in the catalytic hydrogenation of, e.g., C=C double bonds or C≡C triple bonds, carbonyls, nitriles, and isonitriles, or in the catalytic reduction of $NO_2$-groups for the formation of amines. They are furthermore catalytically effective in the hydroformylation reaction, in the synthesis of water gas, the isomerization or cyclization as well as reduction of CO with hydrogen to hydrocarbons, alcohols, or aldehydes.

In addition to that, the new transition metal-complex compounds may be used in an exceptionally effective manner as a coating material on many different surfaces. For this purpose, a carefully cleaned object is dipped into a solution of the particular complex compound to be used, and, if desirable, heated therein. The period of submersion, the level of the selected temperature, as well as the stability of the chosen transition metal-complex compound and its concentration in the solution decide the layer of coating obtainable per unit of time.

In the following, the invention will be more fully described in a number of examples, but is should be understood that these are given only by way of illustration and not by limitation.

EXAMPLE 1

Preparation of $AU_{55}(P(C_6H_5)_3)_{12}Cl_6$

A 250 ml three-neck flask, provided with a stirrer, inside thermometer, gas inlet pipe, and reflux cooler, is charged, under argon as protective gas, with 3.94 g $(C_6H_5)_3PAuCl$ (7.9 mMol.) and 150 ml anhydrous benzene. A moderate stream of diborane is passed through the solution, which immediately turns purple, later dark brown. During the passage, the temperature in the reaction vessel is raised to 50° C. After 30–60 minutes, a dark precipitate forms, whereas the supernatant solution becomes almost colorless. The precipitate is filtered over a reversing frit and dissolved in a small amount of methylene chloride, which leads to formation of a dark red-brown solution; this is filtered once more, whereupon, by addition of benzine, a dark brown substance is precipitated. For further purification, the substance is dissolved in methylene chloride and filtered through a layer of kieselguhr having a thickness of 4 to 5 cm, in order to remove any adhering residues of colloidal gold, if present. A repeated precipitation yields 0.8 g $Au_{55}(P(C_6H_5)_3)_{12}Cl_6$—i.e., 39.0% referring to the amount of triphenylphosphine gold chloride used.

In the course of several days, a further brown-black precipitate is formed, which has not yet been characterized. By filtering the precipitate and adding benzine to the solution, $(C_6H_5)_3P-BH_3$ can be isolated and identified by IR spectrum comparison with authentic specimens, as well as by elementary analysis.

Analysis for gold-complex compound:

Calculated for $Au_{55}(P(C_6H_5)_3)_{12}Cl_6$: C 18.28, H 1.28, Au 76.33, Cl 1.50, P 2.62. Found: C 17.66, H 1.28, Au 76.10, Cl 1.70, P 2.60.

$C_{18}H_{18}BP$ (276.0) Calculated: C 78.26, H 6.52. Found: C 77.22, H 6.54.

Melting point: 180° (lit. 185° C.).

Thermolysis of $Au_{55}(P(C_6H_5)_3)_{12}Cl_6$ 200 mg (0.085 mMol). $Au_{55}(P(C_6H_5)_3)_{12})Cl_6$ are dissolved in 20 ml pyridine and heated to 50° C. for three days. During this time, metallic gold separates partly as a mirror layer and partly in a finely divided dark form, whereas the solution becomes colorless. The weight in gold amounts to 130 mg (calc.: 137 mg).

Structure of the gold-complex compound

The gold complex compound $Au_{55}(P(C_6H_5)_3)_{12}Cl_6$ shows in the Mossbauer-spectrum four different kinds of gold atoms, a metallic gold core, gold atoms coordinated by ligands $P(C_6H_5)_3$— or Cl ligands, respectively, and uncoordinated surface gold. The IR-spectrum shows a shift of the gold-chlorine oscillation from 330 $cm^{-1}((C_6H_5)_3PAuCl)$ to 280 $cm^{-1}$ in the new complex compound.

The molecular weight was determined from the sedimentation coefficient at 15.760 (Calc. 14.195). The osmometric measurement showed a molecular mass of 13.000.

EXAMPLE 2

Preparation of $Rh_{55}(P(C_4H_9)_3{}^t)_{12}Cl_{20}$

A 250 ml three-neck flask, provided with a stirrer, inside thermometer, gas inlet pipe and reflux cooler is charged under argon as protective gas, with 2.0 g $(P(C_4H_9)_3{}^t)_2RhCl$ in 100 ml anhydrous benzene. A uniform gas stream of diborane is passed into the solution and heated simultaneously to 50°-60° C. After about 30 minutes, a dark brown solution forms, which after cooling, is separated from some undissolved matter. The solvent is removed in vacuo and benzine is added to the dark, oily residue. After stirring for several hours, a dark brown solid has formed which is filtered off from the brownish solution. Purification of the solid mass is brought about by dissolving in acetone or chloroform and subsequent precipitation by benzine.

Yield: referring to $((C_4H_9)_3{}^tP)_2RhCl=75\%$ of the theoretical.

EXAMPLE 3

Preparation of $Ru_{55}(P(C_4H_9)_3{}^t)_{12}Cl_{20}$ 0.5 g $RuCl_3 2H_2O$, 2.0 ml $(C_4H_9)_3{}^tP$ and 60 ml tetrahydrofuran are introduced into a 250 ml three-neck flask provided with stirrer, gas inlet pipe, and nitrogen conduit, and reacted with a uniform gas stream of diborane. The solution turns dark brown within 30 to 60 minutes. Subsequently, the solvent is removed by vacuum and the residual oil is treated with benzine, thereby turning into a solid body. The brown-black product is dissolved in acetone, the solution filtered to remove undissolved matter, and, from the acetone solution, black, pyrophoric $Ru_{55}(P(C_4H_9)_3{}^t)_{12}Cl_{20}$ is precipitated by benzine. Yield 60%, referring to ruthenium used.

EXAMPLE 4

Preparation of $Pd_{55}(P(C_4H_9)_3{}^t)_{12}Cl_{20}$ 3.2 g $(P(C_4H_9)_3{}^t)_2PdCl_2$ are dissolved in 150 ml toluene and reacted in a 250 ml three-neck flask provided with reflux cooler, gas inlet pipe, a nitrogen conduit, inside thermometer and stirrer, for 40 minutes at 70° to 80° C. with a uniform gas stream of diborane. The solution formed is dark brown and is filtered off from the solvent after having cooled down. The residue is washed several times with diethyl ether and then dried in vacuo.

Yield 48% of the theoretical, referring to palladium used.

EXAMPLE 5

Preparation of $Ni_{55}(P(OCH_3)_3)_{12}Cl_{20}$

In a 250 ml three-neck flask provided with reflux cooler, gas inlet pipe and a nitrogen conduit, thermometer and magnetic stirrer, 2.0 g anhydrous nickel chloride and 4.0 ml $P(OCH_3)_3$ in 80 ml tetrahydrofuran are reacted at 60° C. with gaseous diborane with careful exclusion of air. The solution turns dark after a time, while a brown-black precipitate is formed. Filtration is carried out, the precipitate is washed with benzene and dried in vacuo.

Yield: 90% pyrophoric $Ni_{55}(P(OCH_3)_3)_{12}Cl_{20}$ referring to nickel used.

EXAMPLE 6

Preparation of $Co_{55}(P(OCH_3)_3)_{12}Cl_{20}$

A three-neck flask provided with reflux cooler, gas inlet pipe, thermometer and magnetic stirrer is reacted under nitrogen with 2.0 g anhydrous $CoCl_2$, 4.0 ml $P(OCH_3)_3$ and 80 ml tetrahydrofuran. Heating to 60° C. is carried out and a uniform gas stream of diborane is passed through the solution. A brown-black precipitate is formed consisting of $Co_{55}(P(OCH_3)_3)_{12}Cl_{20}$, which is filtered off, washed several times with benzene and dried in vacuo.

Yield: 70% of the theoretical.

EXAMPLE 7

Hydrogenation of Hexene-1

50 ml hexene-1, dissolved in tetrahydrofuran, are reacted with hydrogen in a stirring autoclave in the presence of 50 ml $Rh_{55}(P(C_4H_9)_3{}^t)_{12}Cl_{20}$ at a pressure of 70 atm and at room temperature of 20° C. Within 15 to 20 minutes, quantitative hydrogenation takes place with formation of hexane.

EXAMPLE 8

Hydrogenation of Pentene-1

The same procedure as in Example 7 is followed which yields 99.7 vol-% of n-pentane.

EXAMPLE 9

Hydrogenation of Hexine-3

The same procedure as in Example 7 if followed (only at normal pressure of 1 atm) which yields 100 vol-% of n-hexene.

EXAMPLE 10

Hydroformylation of Hexene-1

Hexene-1 is dissolved in tetrahydrofuran, and reacted in a stirring autoclave in the presence of 50 mg $Rh_{55}(P(C_4H_9)_3{}^t)_{12}Cl_{20}$ at 130 atm. with a mixture of hydrogen and carbon monoxide 1:1 at room temperature of 20° C. After a reaction time of 12 hours, an isomer mixture of 25 vol.-% heptanal was measured in the solution by gas-chromatography.

EXAMPLE 11

Hydroformylation of Cyclopentene

The same procedure as in Example 10 was followed, and 22 vol.-% of cyclopentane carbaldehyde were obtained.

EXAMPLE 12

Hydroformylaton of Cyclohexene

The same procedure as in Example 10 was followed (but at a pressure of 150 atm.), resulting in 30 vol.-% cyclohexane carbaldehyde.

EXAMPLE 13

Hydrogenation of Pentene-1

25 ml pentene-1 are added to a solution of 50 mg $Ru_{55}(P(C_4H_9)_3{}^t)_{12}Cl_{20}$ in 2 ml diacetone-alcohol. Hydrogen is passed through the solution at room temperature of 20° C. and normal pressure (1 atm) for 1½ hours. After this time, only n-pentane can be determined by gas chromatography.

EXAMPLE 14

Hydroformylation of Hexene-1

A solution of 50 mg $Ru_{55}(P(C_4H_9)_3{}^t)_{12}Cl_{20}$ in 50 ml tetrahydrofuran is admixed with 50 ml hexene-1. In an autoclave, 75 atm. carbon monoxide and 75 atm hydrogen are added. After a reaction time of 10 hours, 25 vol.-% of heptanal are found as an isometric mixture by gas chromatography.

EXAMPLE 15

Coating by Gold

Objects of glass, plastic, and metal are dipped at room temperature of 20° C. into a solution of $Au_{55}(P(C_6H_5)_3)_{12}Cl_6$ in methylene chloride. Gold coating occurs spontaneously, but the procedure is accelerated by heating. The thickness of the coating layer depends on the time of submersion and the concentration of the solution. The gold-plated surfaces exhibit electric conductivity even in thin layers.

EXAMPLE 16

Gold-coating of Disperse Materials

Disperse materials are coated with gold layers of any desired thinness, by soaking the material, e.g. highly disperse silicic oxide or aluminum oxide in a solution of $Au_{55}(P(C_6H_5)_3)_{12}Cl_6$ in methylene chloride, then filtered off, and dried. Subsequent heating of the material to temperatures above 100° C. leads to decomposition of the complex on the material with the deposition of colloidal gold. Subsequent rinsing with methylene chloride removes other material formed in the decomposition.

While only several examples of the present invention have been shown and described, it is obvious that many changes and modifications may be made thereunto without departing from the spirit and scope of the invention.

What is claimed is:

1. A transition metal-complex compound of the general formula $M_{55}L_{12}X_p$, wherein M is a transition metal of one of the subgroups I, V, VI, VII or VIII of the Periodic System of the elements according to Mendelejeff, L stands for ligands having electron donor properties selected from the group consisting of phosphine and phosphite, X is halogen, and p is equal to 6 to 20.

2. A process for preparing transition metal-complex compounds of the general formula $M_{55}L_{12}X_p$, wherein M is a transition metal of one of the subgroups I, V, VI, VII or VIII of the Periodic System of the elements according to Mendelejeff, L stands for ligands having electron donor properties selected from the group consisting of phosphine and phosphite, X is halogen, and p is equal to 6 to 20, comprising the step of reacting complex compounds of the general formula $L_nMX_m$, in which M, L, and X have the above-defined meanings, n is an integer from 1 to 5, and m is an integer from 1 to 4, with diborane or compounds of the general formula EHRR', wherein E represents boron or aluminum, and R and R' are the same or different and are selected from the group consisting of hydrogen and straight-chain or branched-chain hydrocarbons with 1–10 carbon atoms.

* * * * *